US012589131B2

(12) United States Patent
Prawitt

(10) Patent No.: US 12,589,131 B2
(45) Date of Patent: Mar. 31, 2026

(54) USE OF COLLAGEN HYDROLYSATE IN PREVENTION AND/OR TREATMENT OF FOOD CRAVING

(71) Applicant: ROUSSELOT B.V., Ghent (BE)

(72) Inventor: Janne Prawitt, Ghent (BE)

(73) Assignee: ROUSSELOT B.V., Ghent (BE)

( * ) Notice: Subject to any disclaimer, the term of this patent is extended or adjusted under 35 U.S.C. 154(b) by 0 days.

(21) Appl. No.: 18/834,736

(22) PCT Filed: Feb. 1, 2023

(86) PCT No.: PCT/EP2023/052478
§ 371 (c)(1),
(2) Date: Jul. 31, 2024

(87) PCT Pub. No.: WO2023/148234
PCT Pub. Date: Aug. 10, 2023

(65) Prior Publication Data
US 2025/0114426 A1 Apr. 10, 2025

(30) Foreign Application Priority Data
Feb. 4, 2022 (BE) .................................. 2022/5075

(51) Int. Cl.
*A61K 38/01* (2006.01)
*A61P 3/04* (2006.01)

(52) U.S. Cl.
CPC .............. *A61K 38/014* (2013.01); *A61P 3/04* (2018.01)

(58) Field of Classification Search
None
See application file for complete search history.

(56) References Cited

U.S. PATENT DOCUMENTS

| | | | |
|---|---|---|---|
| 7,897,147 | B2 | 3/2011 | Dadas |
| 8,114,860 | B2 | 2/2012 | Backstrom et al. |
| 9,248,137 | B2 | 2/2016 | Rutenberg et al. |
| 9,309,199 | B2 | 4/2016 | Wolkenberg et al. |
| 10,688,042 | B1 | 6/2020 | Cavallaro |
| 11,141,450 | B2 | 10/2021 | Jimenez del Rio et al. |
| 11,680,066 | B2 | 6/2023 | McKinney |
| 2007/0293427 | A1 | 12/2007 | Vouland et al. |
| 2011/0039767 | A1 | 2/2011 | Nieuwenhuizen et al. |
| 2012/0141448 | A1 | 6/2012 | De Ferra |
| 2014/0113861 | A1 | 4/2014 | Escaich Ferrer et al. |
| 2018/0021411 | A1 | 1/2018 | Losso et al. |
| 2020/0078435 | A1 | 3/2020 | Michaud |
| 2022/0295854 | A1 | 9/2022 | Oesser |

FOREIGN PATENT DOCUMENTS

| | | | | |
|---|---|---|---|---|
| CA | 3074541 A1 * | 9/2021 | ........... | A61K 31/485 |
| CN | 101289507 A | 10/2008 | | |
| CN | 112 813 127 A | 5/2021 | | |
| CN | 113271961 A | 8/2021 | | |
| CN | 113 615 783 A | 11/2021 | | |
| EP | 2 606 904 A1 | 6/2013 | | |
| JP | 2009 235064 A | 10/2009 | | |
| JP | 2012 116773 A | 6/2012 | | |
| JP | 2019-112361 A | 7/2019 | | |
| JP | 2019-529365 A | 10/2019 | | |
| WO | 2020/245299 A1 | 12/2020 | | |
| WO | 2021/156400 A1 | 8/2021 | | |
| WO | 2021/161186 A1 | 8/2021 | | |

OTHER PUBLICATIONS

International Search Report and Written Opinion for WO 2023/148234 (PCT/EP2023/052478), dated May 8, 2023, pp. 1-14.
BE Search Report for BE2022/5075, dated Feb. 4, 2022, pp. 1-13.
International Preliminary Report on Patentability for WO 2023/148234 (PCT/EP2023/052478), dated May 16, 2024, pp. 1-23.
Anonymous: "Peptan collagen peptides", Rousselot, Sep. 1, 2012 (Sep. 1, 2012), pp. 1-33.
Salvatore Luca et al: "Marine collagen and its derivatives: Versatile and sustainable bio-resources for healthcare", Materials Science and Engineering C, Elsevier Science S.A, CH, vol. 113, Apr. 17, 2020 (Apr. 17, 2020).
Lemalab: "How to Get Rid of Sugar Cravings", Aug. 28, 2021 (Aug. 28, 2021), pp. 1-8.
Chinese Office Action for Patent Application No. 202380025162.8, dated Dec. 26, 2024, pp. 1-11 (Translation Included).
Miyab et al. The effect of a hydrolyzed collagen-based supplement on wound healing in patients with burn: A randomized double-blind pilot clinical trial. Burns 46: 156-163, 2020.
Leon-Lopez Arely et al: "Hydrolyzed Collagen-Sources and Applications", Molecules vol. 24, No. 22 Nov. 7, 2019 (Nov. 7, 2019), p. 4031.
Denise Zdzieblik et al: "Collagen peptide supplementation in combination with resistance training improves body composition and increases muscle strength in elderly sarcopenic men: a randomised controlled trial", British Journal of Nutrition, vol. 114, No. 8, Oct. 28, 2015 (Oct. 28, 2015), pp. 1237-1245.
Marra Annachiara et al: "The ABCDEF Bundle in Critical Care", Critical Care Clinics, vol. 33, No. 2, Apr. 1, 2017 (Apr. 1, 2017), pp. 225-243.
Rawal et al. Post-intensive care syndrome: an overview. J Translation Int Med 5(2): 90-92, 2017.
Chinese Office Action for Patent Application No. 202380013782.X, dated Jul. 26, 2024, pp. 1-18 (Translation Included).
(Continued)

*Primary Examiner* — Sudhakar Katakam
*Assistant Examiner* — Zachary J Miknis
(74) *Attorney, Agent, or Firm* — Thomas| Horstemeyer, LLP

(57) ABSTRACT

The present invention relates to the use of collagen hydrolysate in the prevention and/or treatment of food craving. The collagen hydrolysate may have a therapeutic and/or non-therapeutic effect. The prevention and/or treatment of craving by the collagen hydrolysate may find purpose in losing bodyweight or improving general well-being. The collagen hydrolysate is preferably administered as a daily food supplement formulation.

20 Claims, 1 Drawing Sheet

(56) References Cited

OTHER PUBLICATIONS

Japanese Office Action for Patent Application No. 2024-519454, dated Aug. 30, 2024, pp. 1-5 (Translation Included).

Chinese Office Action for Patent Application No. 202380013782.X, dated Oct. 31, 2024, pp. 1-10 (Translation Included).

Jiang Xirui, Novel Biotechnological Fermentation Products, first edition, China Light Industry Press, Aug. 2020, p. 331 (Translation not available).

Hong Hui, Collagen and Collagen Peptides Function and Application, first edition, China Light Industry Press, Jan. 2022, p. 4 (Translation not available).

Harnedy Padraigin A. et al: "Atlantic salmon (*Salmo salar*) co-product-derived protein hydrolysates: A source of antidiabetic peptides", Food Research International, vol. 106, Apr. 1, 2018 (Apr. 1, 2018), pp. 598-606.

Li-Chan Eunice C. Y. et al: "Peptides Derived from Atlantic Salmon Skin Gelatin as Dipeptidyl-peptidase IV Inhibitors", Journal of Agricultural and Food Chemistry, vol. 60, No. 4, Jan. 20, 2012 (Jan. 20, 2012), pp. 973-978.

Colbenson et al. Post-intensive care syndrome: impact. prevention, and management. Breathe 15(2): 98-101, 2019.

Database GNPD [Online] Mintel; Jun. 12, 2018 (Jun. 12, 2018), anonymous: "Joint Pain Relieve Liquid", pp. 1-3.

Kehinde Bababode Adesegun et al: "Recently isolated antidiabetic hydrolysates and peptides from multiple food sources: a review", Critical Reviews in Food Science and Nutrition, vol. 60, No. 2, Nov. 21, 2018 (Nov. 21, 2018), pp. 322-340.

Adrian Meule. Assessment of Food Cravings. In J. Ifland, M. T. Marcus, & H. G. Preuss (Eds.), Processed Food Addiction: Foundations, Assessment, and Recovery, 1 ed., pp. 137-145, Taylor & Francis.

Rodriguez-Martin et al. Front Psychol. 2015; 6: 21.

Pelchat ML et al. Physiol Behav. Jan. 2000; 68(3):353-9.

Kemps et al. Current Directions in Psychological Science, 19(2), 86-90).

* cited by examiner

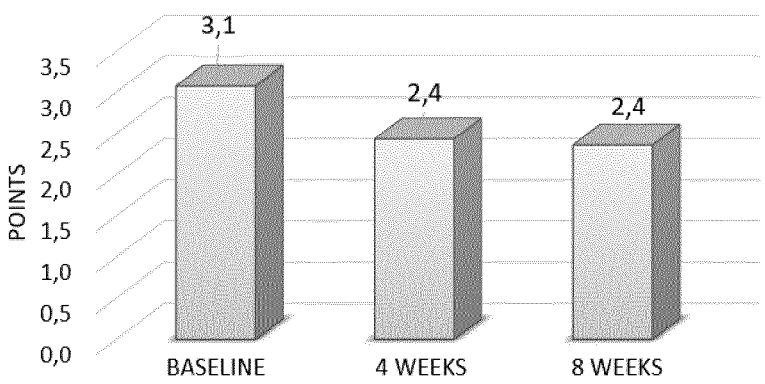

USE OF COLLAGEN HYDROLYSATE IN PREVENTION AND/OR TREATMENT OF FOOD CRAVING

CROSS-REFERENCE TO RELATED APPLICATIONS

This application is the National Stage of International Application No. PCT/EP2023/052478, filed Feb. 1, 2023, which claims priority to BE2022/5075, filed Feb. 4, 2022, all of which are entirely incorporated herein by reference.

TECHNICAL FIELD

The current invention relates to a method for prevention and/or treatment of food craving, in particular to a food supplement for prevention and/or treatment of food craving.

BACKGROUND OF THE INVENTION

Food craving is an intense desire to eat specific food(s). The intensity and specificity in food craving distinguishes it from ordinary hunger. Food craving is considered to have cognitive (e.g. strong thoughts about food), emotional (e.g. changes in mood), behavioural (e.g. seeking for food), and physiological (e.g. salivation) characteristics (Rodriguez-Martin et al. Front Psychol. 2015; 6:21). Women are more likely to experience food cravings than men, which may be related to hormonal differences between women and men. Food craving can be triggered by a specific mood state and can be triggered by environmental cues, such as stress (Cepeda-Benito et al. Behav Res Ther. 2000 November; 38 (11): 1125-38). Food cravings typically occur in the late afternoon and/or the evening.

Food craving is considered to be a rather different condition than a feeling of hunger. In contrast to feeling of hunger, food craving is not necessarily associated with food deprivation and an empty stomach (Pelchat M L et al. Physiol Behav. 2000 January; 68 (3): 353-9). Food cravings are usually not alleviated by intake of foods in general. Instead a strong desire for energy-dense foods, particularly foods having high amounts of sugar, fat, and/or carbohydrates. Exposing a subject to tempting food-cues does not induce food craving, which also indicates that food craving is different from a feeling of hunger (Grubliauskiene et al. Front. Psychol. 5:788). Although food craving and a feeling of hunger can co-exist, hunger is not considered to be a prerequisite for experiencing a food craving.

Excessive food craving can lead to health and psychological risks (Kemps et al. Current Directions in Psychological Science, 19(2), 86-90). Overeating leads to an increase in body mass index and obesity, insulin resistance, and other health problems. Overeating also has psychological consequences, such as feeling of guilt, shame and depression. However, food craving is not always pathological. Food craving can naturally disappear or alleviate over time, which may or may not include occasional flare-ups. In other words, food craving is not always a chronic condition. Food craving also does not always have to lead to other health problems, particularly in less extreme forms of food craving. Nevertheless, healthy individuals or individuals experiencing a less extreme form of food craving may benefit from measures for preventing and/or treating food craving by maintaining or improving their aesthetic body appearance and/or by improving their general functioning and well-being.

Food craving can occur in healthy individuals, but food cravings may be more frequent or intense in certain medical conditions including but not limited to obesity, pregnancy, gastrointestinal disorders, Addison's disease, premenstrual syndrome, hormonal imbalance, hyperthyroidism, stress, polyphagia, low serotonin, cystic fibrosis, and liver disease. In these aforementioned medical conditions, food craving can be considered a symptom of the underlying medical condition, although generally unrelated from the pathophysiology of the underling condition. It appears that the biological mechanisms of food craving may be different in healthy individuals and individuals suffering one of said medical conditions. For instance, it has been shown that thalamic brain activation plays a more prominent role in food craving in obese individuals as compared to lean individuals (Jastreboff et al. Diabetes Care (2013) 36:394-402).

Adequate measures to prevent and/or treat food craving are desired, both in a pathological (therapeutic) and in a non-pathological (non-therapeutic, e.g. a cosmetic effect, improving general functioning, improving well-being) context.

It has been proposed to reduce food craving by means of appetite suppression. Appetite suppression has mostly been realized with appetite suppressant drugs that act via brain catecholamine pathways or via serotonin pathways (Silverstone et al. Drugs volume 43, pages 820-836, 1992). Appetite suppressant drugs include amphetamines, antidepressants, and drugs which enhance serotonin activity. These appetite suppressant drugs have several limitations. First, they are considered to have unacceptable side effects. Second, as prescription medications, appetite suppressant drugs are not appropriate for use in healthy (e.g. non-obese) individuals. Third, appetite suppressant drugs do not selectively target food craving, hence they reduce the general appetite and impair the normal food intake. Fourth, it is difficult to appropriately time the intake of an appetite suppressant to effectively reduce food craving, since food craving may not always occur at the same time or moment of the day. A subject may typically take in an appetite suppressant once the food craving already manifests itself, hence the intake of the appetite suppressant may be delayed or too late to effectively prevent and/or treat food craving.

There remains an unmet need for a method that prevents and/or treats food cravings. In particularly, there is a desire for a method that is considered to be safe and that may be applied as a therapeutic or a non-therapeutic method. Moreover, there is a desire for a method that more specifically targets overeating in food craving, e.g. does not suppress normal feeling of hunger and/or does not impair the normal food diet. On the one hand, it may be beneficial to suppress craving without affecting the normal appetite, e.g. in healthy normal weight individuals that are not necessarily seeking weight reduction. On the other hand, it could be beneficial in overweight or obese individuals to reduce normal food intake too, in addition to reduction in craving. There is also a desire for a method that prevents and/or treats food craving, and which is less or not dependent on the timing of when the method is applied. There is also a desire for a method for the prevention and/or treatment of food craving, and which does not cause the undesired side-effects of the commonly applied appetite suppressing drugs.

The present invention aims to provide such a method.

SUMMARY OF THE INVENTION

The inventors discovered that collagen hydrolysate supplementation prevents and/or treats food craving.

In one aspect, the current invention relates to the use of collagen hydrolysate in non-therapeutic prevention and/or treatment of food craving.

In one aspect, the current invention relates to the use of collagen hydrolysate in therapeutic prevention and/or treatment of food craving.

In one aspect, the current invention relates to a method of treating subjects experiencing food craving using collagen hydrolysate.

In one aspect, the current invention relates to the use of collagen hydrolysate for the manufacture of a medicament for preventing and/or treating food craving.

Several findings of the inventors show that the prevention and/or treatment of food craving by collagen hydrolysate is not necessarily mediated by reducing hunger and/or increasing satiation. First, the inventors found that food craving is prevented and/or treated particularly after repeated (daily) intake of collagen hydrolysate. Second, the inventors found that food craving is prevented and/or treated in subjects without affecting their normal food routine, such as their normal intake of meals. Third, the inventors found no clear correlation between the timing of collagen hydrolysate intake and the prevention and/or treatment of food craving.

Without being bound by theory, the present inventors find that the dosage regimen can play a role in the management of craving. This (if desired) allows for further specific reduction in craving, without affecting normal appetite. For instance, specific reduction in craving highest if total daily dose of collagen hydrolysate is not too high (e.g. not more than 40 g daily dose), and divided over two or more unit doses (e.g. unit dose each not more than 20 g, preferably ~10 g.) Moreover, a specific reduction in craving is highest when the collagen hydrolysate is taken once every other day or daily. A molecular weight of the collagen hydrolysate below 9000 Da seems beneficial for specific reduction in craving. Without being bound by theory, the present inventors consider that a larger molecular weight creates a larger feeling of fullness and therefore leads to larger suppression of normal appetite, without necessarily further reducing craving.

DETAILED DESCRIPTION OF THE INVENTION

In one aspect, the current invention relates to the use of collagen hydrolysate in non-therapeutic prevention and/or treatment of food craving.

In one aspect, the current invention relates to the use of collagen hydrolysate in therapeutic prevention and/or treatment of food craving.

Benefits and advantages of the present invention are:

The use of collagen hydrolysate, for instance as daily supplement, is generally considered safe;

The use of collagen hydrolysate in the prevention and/or treatment of food craving is applied both as a therapeutic or a non-therapeutic method;

The use of collagen hydrolysate in the prevention and/or treatment of food craving does not necessarily impair the normal food intake, and does not necessarily suppress the normal feeling of hunger or appetite (e.g. food craving is more specifically targeted than use of appetite suppressants). This is particularly beneficial in healthy normal weight individuals that are not necessarily seeking weight reduction. In overweight or obese individuals, lower intake of normal food may be beneficial too in addition to reduction in craving;

The use of collagen hydrolysate in the prevention and/or treatment of food craving is relatively independent (e.g. as compared to the use of appetite suppressant) on the timing of when it is applied. A subject may typically take the collagen hydrolysate before the food craving manifests itself and thereby more effectively prevent and/or treat food craving;

The prevention and/or treatment in food craving by collagen hydrolysate was found to be durable, since less food craving was seen at both 4 weeks and 8 weeks after commencing collagen hydrolysate supplementation.

Prevention and/or Treatment of Food Craving

As used herein, the term "food craving" is an intense desire to eat a particular type of food, generally a food with a specific calorie-density (e.g. calorie-dense), texture and/or flavour. The experience of a food craving is considered to be multidimensional. Physiologically, food craving may prepare the body for ingestion of food, as shown by increased salivary flow and activation of reward-related brain areas such as the striatum. Food craving may often also comprise cognitive (i.e., excessive thinking about the food) and emotional (e.g. changes in mood) components. Food craving may often also include a behavioural component, including excessive seeking for food (Meule et al. Current Nutrition Reports volume 9, pages 251-257, 2020). Food craving generally increases throughout the day. Food cravings most typically occur in the late afternoon and/or the evening, for instance after the evening meal or at night. Food craving is generally not alleviated by intake of regular meals (e.g. breakfast, lunch, dinner). Food craving is considered to be different from hunger. Whereas hunger is typically the result of an empty stomach, food craving is typically not the result of an empty stomach. Whereas hunger is typically alleviated by consumption of any type of food, food craving is typically alleviated by calorie-dense foods. Whereas hunger is typically correlated to the length of a food deprivation, food craving typically is not correlated to food deprivation or the length of a food deprivation. It is typically considered that a subject experiences food craving (and not hunger), if said subject has a desire for food, preferably an intense desire for food, within 1 to 1.5 hours of consuming a meal (e.g. a normal breakfast, lunch or dinner). Whereas hunger usually comes with specific physical symptoms associated with food deprivation and/or an empty stomach (e.g. stomach growling and/or dizziness), this is usually not the case for food craving. In addition or alternatively, "food craving" is considered to be differentiated from hunger through its intensity, that is, food craving is a more intense or extreme form of desire for food. Hunger and food craving can co-exist, however hunger is not considered not to be a prerequisite for experiencing a food craving.

As used herein, "hunger" refers to the absence of fullness or satiation and is generally the result of an empty stomach. Hunger is generally alleviated by consumption of any type of food, including a calorie-dense or a non-calorie-dense food. Hunger is generally correlated to a length of food deprivation, i.e. the longer the food deprivation, the higher the feeling of hunger. Hunger usually comes with specific physical symptoms associated with food deprivation and/or an empty stomach, for instance stomach growling and/or dizziness. These symptoms typically decrease or disappear after eating.

In an embodiment, "food craving" as disclosed herein is not the same, or is independent of (feeling of) hunger.

In an embodiment, "food craving" as disclosed herein is not the same, or is independent of (feeling of) satiation.

In an embodiment, "food craving" as disclosed herein is independent of food deprivation.

In an embodiment, "food craving" as disclosed herein is independent of the length of a food deprivation.

In an embodiment, "food craving" as disclosed herein is independent of physical symptoms, preferably independent of physical symptoms associated with food deprivation and/or an empty stomach (for instance stomach growling and/or dizziness).

In an embodiment, "food craving" as disclosed herein is independent of filling of the stomach.

In an embodiment, "food craving" as disclosed herein is an increased desire for food in the late afternoon, the evening, and/or the night.

In an embodiment, "food craving" as disclosed herein is a desire for a calorie-dense food.

In an embodiment, "food craving" as disclosed herein is independent of a desire for a food which is not a calorie-dense food.

In an embodiment, "food craving" as disclosed herein is independent of a desire and/or the intake of a nutrient-rich food.

In a preferred embodiment, "food craving" as disclosed herein is a desire for food within 3 hours, preferably within 1.5 hours, more preferably within 1 hour, after a meal.

In a preferred embodiment, the use of collagen hydrolysate as disclosed herein comprises a use in food craving that is a craving for a calorie-dense food.

The inventors found that food craving may be prevented and/or treated without impairing the normal food intake such as the normal intake of meals.

In a preferred embodiment, the use of collagen hydrolysate as disclosed herein comprises preventing and/or treating food craving independent of a reduced hunger and/or an increased satiation.

In a preferred embodiment, the use of collagen hydrolysate as disclosed herein comprises preventing and/or treating food craving independent of the normal intake of meals.

In an embodiment, the food craving as disclosed herein is characterised by a preference for calorie-dense foods over nutrient-rich foods.

As used herein, a "calorie-dense food" means a food that has a high amount of calories relative to its weight. The high density of calorie is typically due to a high concentration of saturated fat, added sugars, and/or other simple carbohydrates. A "calorie-dense food" herein contains preferably more than 100 kcal per 100 g weight of the food, more preferably more than 200 kcal per 100 g weight, most preferably more than 300 kcal per 100 g weight. A calorie-dense food may, in addition or alternatively, mean a food with more than 10 g sugar, preferably with more than 25 g sugar, more preferably with more than 50 g sugar, per 100 g weight of the food. In addition or alternatively, a calorie-dense food may mean a food with more than 10 g saturated fat, preferably with more than 25 g saturated fat, more preferably with more than 50 g saturated fat, per 100 g weight of the food. The "calorie-dense food" herein is preferably not a nutrient-rich food.

The calorie-dense food as disclosed herein may be one or more selected from the group comprising processed food, fried food, potato fries, pizza, fast-food, candy, chips, pastry, cake, ice-cream, chocolate, fast-food, nuts, butter, cream, cheese, bacon, sausages, sauces, condiments, dressings, and sugary drink.

As used herein, a "nutrient-rich food" is a food with a high nutritional value (e.g. per energy content and/or weight). Several indicators for nutrient density of a food are available. For instance, Nutrient Rich Food (NRF) index scores are used to determine nutrient profiles and are based on nutrient density. Nutrient density is the ratio of the nutrient composition of a food to the nutrient requirements of the human consumer. The development of NRF index scores typically involves several methodological issues, including the selection of key nutrients, the choice of recommended daily allowances (RDA), and the basis of calculation (per 100 g, 100 kcal (418 kJ), or portion sizes). The median NRF9.3 Index score is NRF index score known by the skilled person. A higher NRF index scores denotes a higher nutrient density per 100 kcal (Drewnowski et al. Am J Clin Nutr. 2010 April; 914): 1095S-1101S). A "nutrient-rich food" as disclosed herein preferably means that the food has a median NRF9.3 Index score higher than 0, preferably higher than 20, more preferably higher than 40, all per 100 kcal food.

As used herein, a "meal" refers to a eating occasion that takes place at a certain time and includes prepared food. Meals occur on a daily basis, typically several times a day. Breakfast, lunch, and dinner are considered to be meals. A meal is typically considered to comprise eating a reasonably large amount of food (e.g. 500-1000 kcal per meal). Intake of a meal typically decreases the feeling of hunger, increases satiation, and induces satiety.

Non-Therapeutic and Therapeutic Prevention and/or Treatment of Food Craving

The collagen hydrolysate as disclosed herein can have both a non-therapeutic and a therapeutic use in the prevention and/or the treatment of food craving. The non-therapeutic or therapeutic uses can be separated based on nature of the food craving and/or the distinct groups of subjects experiencing the food craving.

The first group (herein the "group of healthy subjects") comprises healthy persons who do not receive therapeutic benefit from the treatment with collagen hydrolysate as disclosed herein. For example, the food craving may be non-pathological, meaning that the food craving generally has a severity that is not expected to lead to health issues and wherein the food craving does not lead to symptoms of pain and suffering. In addition or alternatively, the food craving may have a nature or severity such that it naturally disappears over time (i.e. it is not chronic). In addition or alternatively, the severity of the food craving in the group of healthy subjects is limited, such that they would generally not seek help from a professional medical practitioner. The group of healthy subjects may need less or shorter treatment with collagen hydrolysate to prevent and/or treat the food craving, as compared to subjects wherein the food craving is of a pathological nature. The collagen hydrolysate as disclosed herein may improve the general performance of the group of healthy subjects. In the group of healthy subjects, the collagen hydrolysate as disclosed herein may achieve one or more of the following effects:

improving aesthetic appearance of the body (e.g. as a cosmetic to promote slimming);

losing body weight;

reducing body mass index;

reducing food seeking events;

increasing productivity in daily life;

improving self-esteem;

reducing feeling of guilt;

reducing feeling of shame;

improving general functioning and/or well-being; and reducing non-pathological conditions due to overeating and/or eating calorie-dense foods, for instance one or more non-pathological conditions selected from the group comprising: cramping, abdominal pain, bloating, gas formation, diarrhoea, constipation.

The second group (herein the "group of pathological subjects") comprises subjects wherein the food craving is of a pathological nature, meaning that the food craving leads to symptoms of pain and suffering, and/or may lead to (serious) health and psychological risks. The severity of the food craving is such that help from a professional medical practitioner is generally sought for. The group of pathological subjects may require more or longer treatment with collagen hydrolysate for prevention and/or treatment of food craving, as compared to wherein the food craving is of a non-pathological nature. In the group of pathological subjects, the food craving can be the primary or the only pathology. Alternatively, the food craving may be a symptom of an underlying disease, thus wherein the food craving is not the primary or the only pathology. For instance, the group of pathological subjects comprises patients with gastrointestinal disorder, obesity, Addison's disease, premenstrual syndrome, hormonal imbalance, hyperthyroidism, stress, polyphagia, low serotonin, cystic fibrosis, or liver disease, and wherein food craving is a symptom (of the one or more possible symptoms). The treatment of these subjects with collagen hydrolysate may generally treat the food craving as (one of many of the) symptoms, without further affecting the underlying disease or pathophysiology.

The professional medical practitioner is typically able to determine on a case-by-case basis whether events of food craving require a therapeutic or a non-therapeutic intervention (i.e. whether a person falls in the group of healthy subjects or in the group of pathological subjects). The professional medical practitioner may for instance establish whether the food craving may lead to (serious) health and psychological risks. The professional medical practitioner may, in addition or alternatively, establish whether the food craving is a symptom of a underlying medical condition.

In an embodiment, the use of collagen hydrolysate as disclosed herein is non-therapeutic. In an embodiment, the use of collagen hydrolysate as disclosed herein is cosmetic. In an embodiment, the use of collagen hydrolysate as disclosed herein is in a healthy subject. In an embodiment, the food craving as disclosed herein is not a symptom of an underlying medical condition (pathology). In an embodiment, the use of collagen hydrolysate as disclosed herein is for food craving that is not chronic and/or naturally disappears. In an embodiment, the use of collagen hydrolysate as disclosed herein is for food craving that is not of an extreme form and/or or is not associated with further symptoms, disease and/or health issues. In an embodiment, the use of collagen hydrolysate as disclosed herein is for food craving that is not of a pathological nature.

In an embodiment, the use of collagen hydrolysate as disclosed herein is in a group of healthy subjects as disclosed herein.

In an embodiment, the use of the collagen hydrolysate as disclosed herein is for one or more selected from the group comprising:
  reducing body mass index;
  reducing food seeking events;
  increasing productivity in daily life;
  improving self-esteem;
  reducing feeling of guilt;
  improving general functioning and/or well-being; and
  reducing non-pathological conditions due to overeating and/or eating calorie-dense foods, for instance one or more non-pathological conditions selected from the group comprising: cramping, abdominal pain, bloating, gas formation, diarrhoea, constipation.

In a preferred embodiment, the collagen hydrolysate as disclosed herein is for (therapeutic) use in the prevention and/or treatment of food craving.

In a preferred embodiment, the food craving that is therapeutically targeted is a symptom in one or more conditions selected from the group comprising gastrointestinal disorder, obesity, Addison's disease, premenstrual syndrome, hormonal imbalance, hyperthyroidism, stress, polyphagia, low serotonin, cystic fibrosis, and liver disease.

In an embodiment, the use of collagen hydrolysate as disclosed herein is in a group of pathological subjects as disclosed herein.

In an embodiment, the use of collagen hydrolysate for preventing and/or treating food craving as disclosed herein is in a patient suffering one or more conditions selected from the group comprising gastrointestinal disorder, obesity, Addison's disease, premenstrual syndrome, hormonal imbalance, hyperthyroidism, stress, polyphagia, low serotonin, cystic fibrosis, and liver disease.

As used herein, "obesity" refers to a medical condition in which excess body fat has accumulated to the extent that it may have an adverse effect on health. Obesity isn't just a cosmetic concern. Obesity is a medical problem since it increases the risk of other diseases and health problems, such as heart disease, diabetes, high blood pressure and certain cancers. The professional medical practitioner may establish by one or more means whether a person is obese. Generally, a body mass index (BMI) of 30.0 or higher is considered to indicate the presence of obesity. Reducing body fat and/or BMI in an obese individual is herein considered to be a therapeutic intervention. In the current disclosure, a BMI of 25.0 to <30 indicates a person being overweight. "Overweight" as used herein refers to a non-medical condition characterized by excess accumulation of body fat. Reducing body fat and/or BMI in an overweight individual is herein considered to be a non-therapeutic intervention.

The collagen hydrolysate as disclosed herein may be suitable for preventing and/or treating craving in one or more groups of subjects selected from the group comprising:
  subjects that have healthy weight;
  subjects that are overweight; and
  subjects that are obese.

The collagen hydrolysate as disclosed herein may be suitable for preventing and/or treating craving in a range of subjects having different BMI.

In an embodiment, the prevention and/or treatment of food craving as disclosed herein is in a subject with a BMI of less than 25, e.g. a BMI of 15-25, or 20-25.

In an embodiment, the prevention and/or treatment of food craving as disclosed herein is in a subject with a BMI of 25-30.

In an embodiment, the prevention and/or treatment of food craving as disclosed herein is in a subject with a BMI of 30 or higher, e.g. a BMI of 30-50, or 30-40, or 30-35.

In one aspect, the current invention relates to a method, preferably a therapeutic method, for the prevention and/or treatment of food craving. The method as disclosed herein may be used in subjects already experiencing food craving (e.g. as a method for the treatment of the subject), or may be used in subjects not experiencing food craving yet (e.g. as a method for the prevention of food craving). The method of prevention and/or treatment may comprise one or more features of the embodiments described herein for the use of collagen hydrolysate in the prevention and/or treatment of food craving, including the type(s) of collagen hydrolysate for the use as disclosed herein, the formulation(s) of collagen hydrolysate for the use as disclosed herein, the timing(s) of collagen hydrolysate administration or intake for the use as disclosed herein, and the dosing(s) of collagen hydrolysate administration or intake (e.g. dosage regimens, unit doses, daily doses) for the use as disclosed herein. The method of prevention and/or treatment as disclosed herein may be suitable for treating subjects with one or more less extreme forms of food craving as disclosed herein (e.g. requiring non-therapeutic intervention). The method of prevention and/or treatment may, in addition or alternatively, be suitable for treating subjects with one or more extreme forms of food craving and/or wherein the food craving may lead to (serious) health and psychological risks as disclosed herein (e.g. requiring therapeutic intervention).

In one aspect, the current invention relates to the use of collagen hydrolysate as disclosed herein for the manufacture of a medicament for the prevention and/or treatment of food craving. The use of collagen hydrolysate for the manufacture of a medicament as disclosed herein may comprise one or more features of the embodiments described herein for the use of collagen hydrolysate in the prevention and/or treatment of food craving, including the type(s) of collagen hydrolysate for the use as disclosed herein, the formulation(s) of collagen hydrolysate for the use as disclosed herein, the timing(s) of collagen hydrolysate administration or intake for the use as disclosed herein, and the dosing(s) of collagen hydrolysate administration or intake (e.g. dosage regimens, unit doses, daily doses daily amounts) for the use as disclosed herein. The medicament comprising collagen hydrolysate may be suitable for treating subjects with one or more less extreme forms of food craving as disclosed herein (e.g. requiring non-therapeutic intervention). The medicament comprising collagen hydrolysate may, in addition or alternatively, be suitable for treating subjects with one or more extreme forms of food craving and/or wherein the food craving may lead to (serious) health and psychological risks as disclosed herein (e.g. requiring therapeutic intervention).

Collagen Hydrolysate

As used herein, a "collagen hydrolysate" is a mix of short chains of amino acids derived from native collagen, generally via hydrolysis steps, including enzymatic hydrolysis (also called enzymatic hydrolysation). The degree of hydrolysis usually has an impact on the average molecular weight of the final product. A collagen hydrolysate typically has a molecular weight of 1-10 kDa (Dalton). The term "collagen hydrolysate" may be used interchangeably and synonymous with the terms "hydrolysed collagen" or "collagen peptide".

The collagen hydrolysate as disclosed herein may be derived from one or more types of collagen selected from the group comprising type I collagen, type II collagen, and type III collagen. In addition or alternatively, the collagen hydrolysate as disclosed herein may be a mixture of one or more of type I, type II, and type III collagen.

The collagen hydrolysate as disclosed herein is preferably derived from collagen type I and/or collagen type II. In addition or alternatively, the collagen hydrolysate as disclosed herein is preferably derived from animal raw material that comprises mostly collagen type I and/or collagen type II as the collagen therein.

The collagen hydrolysate as part of the current invention may comprise collagen which is hydrolysed or partially hydrolysed, wherein the collagen may be derived from any species of animal. An animal herein may refer to any animal capable of providing connective tissue and wherein the connective tissue can be used to prepare collagen hydrolysate.

In an embodiment, the collagen as taught herein is derived from a cow. In an embodiment, the collagen as taught herein is derived from a pig. In an embodiment, the collagen as taught herein is derived from a fish.

In various embodiments, the collagen as disclosed herein is a mixture of collagen from different sources, such as collagen originating from multiple animal species, and/or collagen originating from different tissues. For example, the collagen as disclosed herein may be a mixture of two or more collagens chosen the group comprising fish collagen, porcine collagen, and bovine collagen. In addition or alternatively, the collagen may be a mixture of collagen chosen from skin-, cartilage-, bone-, and/or connective tissue-derived collagen.

"Hide" is generally used to refer to the outer covering of large animals such as from the bovine group or any other large animals. "Skin" is generally used to refer to the outer covering of small animals like deer, goat, sheep, etc. The terms "skin" and "hide" may herein be used interchangeably, and may refer the outer coverage of an animal, irrespective of size.

The "connective tissue" as disclosed herein can be one or more types chosen form the group comprising connective tissue from the corpus callosum, skin, antler, protrusions (e.g. humps) horns, head, brain, neck, ear, eye, nose, tongue, lip, mouth, oesophagus, trachea, limbs, feet, toes, palms, claws, bones, cartilage, bone marrow, joints, membranes, hind, ligaments, tendon, rib, diaphragm, muscle, skeletal muscle, smooth muscle, intestine, venetian, blood vessels, bladder, stomach, aorta, heart, liver, kidney, chest, lung, spleen, pancreas, egg, sperm, testis, ovary, nerve, gallbladder, and belly.

In a preferred embodiment, the collagen as taught herein is derived from the skin and/or skin connective tissue. In another preferred embodiment, the collagen as taught herein is derived from cartilage. In yet another preferred embodiment, the collagen as taught herein is derived from bone.

The collagen as disclosed herein may be a mixture of collagens derived from two or more tissues and/or two or more animals. In an embodiment, the collagen as disclosed herein is a mixture of two or more collagens selected from the group comprising skin collagen, cartilage collagen, and bone collagen.

In various embodiments of the current invention, the collagen hydrolysate may be produced by the enzymatic hydrolysis or partial enzymatic hydrolysis of collagen, wherein the enzyme used for this purpose may be one or more selected from the group comprising serine protease, alkaline protease, neutral protease, flavour protease, complex protease, thiol protease, bromelain, metalloprotease, aspartame, protease, carboxypeptidase, pepsin, chymotrypsin, trypsin, cathepsin K, chymotrypsin, papain, and subtilisin.

The molecular weight as disclosed herein is preferably the mean (averaged) molecular weight, more preferably the weight average molecular weight (Mw).

The collagen hydrolysate as disclosed herein may have a mean molecular weight of at least 100 Da, 200 Da, 300 Da, 400 Da, 500 Da, 1000 Da, 1500 Da, 2000 Da, 2500 Da, 3000 Da, 3500 Da, 4000 Da, 4500 Da, 5000 Da, 5500 Da, 6000 Da, 6500 Da, 7000 Da, 7500 Da, 8000 Da, 8500 Da, 9000 Da, 9500 Da, or 10000 Da. In addition or alternatively, the collagen hydrolysate as disclosed herein may have a mean molecular weight of no more than 10000 Da, 9500 Da, 9000

Da, 8500 Da, 8000 Da, 7500 Da, 7000 Da, 6500 Da, 6000 Da, 5500 Da, 5000 Da, 4500 Da, 4000 Da, 3500 Da, 3000 Da, 2500 Da, 2000 Da, 1500 Da, 1000 Da, 500 Da, 400 Da, 300 Da, 200 Da, or 100 Da.

In a preferred embodiment, the collagen hydrolysate as disclosed herein has a mean molecular weight between 1500 Da and 6000 Da.

It is beneficial in the context of the current invention if the collagen hydrolysate has an average molecular weight of below 9000 Da, for instance 1500-6000 Da. For example, the present inventors find a reduction in craving for collagen hydrolysates with an average molecular weight of ~2000 Da, ~5000 Da, or ~9000 Da, but the highest reduction in craving is seen when the average molecular weight is 2000 Da or 5000 Da.

The collagen hydrolysate as disclosed herein may have a mean molecular weight between 300 Da and 10000 Da, e.g. between 500 Da and 7500 Da, between 1000 Da and 6000 Da, between 1500 Da and 5000 Da, or between 1500 Da and 3000 Da.

In an embodiment, the collagen hydrolysate as disclosed herein has a mean molecular weight between 1250 Da and 2750 Da, preferably between 1500 Da and 2500 Da, more preferably between 1750 Da and 2250 Da.

In an embodiment, the collagen hydrolysate as disclosed herein has a mean molecular weight of between 4250 Da and 5750 Da, preferably between 4500 Da and 5500 Da, more preferably between 4750 Da and 5250 Da.

In an embodiment, the collagen hydrolysate as disclosed herein has a mean molecular weight of between 2000 Da and 5000 Da, preferably between 2500 Da and 4500 Da, more preferably between 3000 Da and 4000 Da.

In an embodiment, the collagen hydrolysate as disclosed herein has a mean molecular weight between 1500 Da and 3000 Da or a mean molecular weight between 3000 Da and 6000 Da.

In an embodiment, the collagen hydrolysate as disclosed herein has a protein content of 75-99 wt. %, preferably 80-99 wt. %, more preferably 85-99 wt. %, most preferably 90-99 wt. % (e.g. 95-99%).

In an embodiment, the collagen hydrolysate as disclosed herein comprises glycine in an amount of 15-25 wt. %, proline in an amount of 9-18 wt. %, and hydroxyproline in an amount of 6-15 wt. %, all per total weight of the amino acids in the collagen hydrolysate.

In an embodiment, the collagen hydrolysate as disclosed herein comprises glycine in an amount of 5-50 wt. %, preferably in an amount of 10-30 wt. %, more preferably in an amount of 12.5-27.5 wt. %, even more preferably in an amount of 15-25 wt. %, most preferably in an amount of 17.5-22.5 wt. %, all per total weight of the amino acids in the collagen hydrolysate.

In an embodiment, the collagen hydrolysate as disclosed herein comprises proline in an amount of 2-25 wt. %, preferably in an amount of 7-20 wt. %, more preferably in an amount of 9-18 wt. %, most preferably in an amount of 12-15 wt. %, all per total weight of the amino acids in the collagen hydrolysate.

In an embodiment, the collagen hydrolysate as disclosed herein comprises hydroxyproline in an amount of 2-20 wt. %, preferably in an amount of 7-18 wt. %, more preferably in an amount of 6-15 wt. %, most preferably in an amount of 9-12 wt. %, all per total weight of the amino acids in the collagen hydrolysate.

In an embodiment, the collagen hydrolysate as disclosed herein has a molecular weight of 1750-2250 Da and comprises glycine in an amount of 15-25 wt. %, proline in an amount of 9-18 wt. %, and hydroxyproline in an amount of 6-15 wt. %, all per total weight of the amino acids in the collagen hydrolysate.

In an embodiment, the collagen hydrolysate as disclosed herein has a molecular weight of 4750-5250 Da and comprises glycine in an amount of 15-25 wt. %, proline in an amount of 9-18 wt. %, and hydroxyproline in an amount of 6-15 wt. %, all per total weight of the amino acids in the collagen hydrolysate.

In an embodiment, the collagen hydrolysate as disclosed herein has a molecular weight of between 1500-3000 Da and comprises glycine in an amount of 15-25 wt. %, proline in an amount of 8-18 wt. %, and hydroxyproline in an amount of 6-15 wt. %, all per total weight of the amino acids in the collagen hydrolysate.

Formulation of Collagen Hydrolysate

The collagen hydrolysate as disclosed herein may be provided in a food formulation, food supplement formulation, or pharmaceutical formulation, preferably a food supplement formulation.

The collagen hydrolysate as disclosed herein may be provided in a solid dosage form such as a capsule, a tablet, or a powder, preferably a powder.

The collagen hydrolysate as disclosed herein may be provided in a formulation such as a drinkable solution or suspension, drink such as beer, syrup, artificially-flavoured drink, carbonated beverage, (water-soluble) powdered mixture, (water-soluble) paste, (water-soluble) powder, (water-soluble) tablet, (water-soluble) pill, (water-soluble) dragee, (water-soluble) caplet, (water-soluble) sachet, or (water-soluble) capsule. In addition or alternatively, the collagen hydrolysate as disclosed herein may be present in a functional food, e.g. a juice, shake, dairy drink, yoghurt, yoghurt drink, dessert, energy bar, nutritional bar, slimming bar, or confectionery such as gummies or center-filled gummies.

Timing of Collagen Hydrolysate Administration or Intake

In an embodiment, the collagen hydrolysate as disclosed is administered not later than 2 hours, preferably not later than 4 hours, more preferably not later than 6 hours, prior to a meal.

In an embodiment, the collagen hydrolysate as disclosed herein is administered repeatedly to a subject.

In an embodiment, the collagen hydrolysate as disclosed herein is administered to a subject every day.

In an embodiment, the collagen hydrolysate as disclosed is administered to a subject for at least two consecutive weeks, more preferably at least four consecutive weeks, even more preferably at least six consecutive week, most preferably at least eight consecutive weeks.

The collagen hydrolysate as disclosed herein may be administered daily, once every other day, thrice weekly, twice weekly, or weekly. In addition or alternatively, the collagen hydrolysate as disclosed herein may be administered once a day, twice a day, or three times a day. In addition or alternatively, the collagen hydrolysate as disclosed herein may be administered for at least 1 day, or for at least 2 days, or for at least 3 days, or for at least 4 days, or for at least 5 days, or for at least 6 days, or for at least 1 week, or for at least 2 weeks, or for at least 3 weeks, or for at least 4 weeks, or for at least 5 weeks, or for at least 6 weeks, or for at least 8 weeks, or for at least 12 weeks, or for at least 16 weeks.

The inventors found that collagen hydrolysate may prevent and/or treat food craving independent of the timing of when it is administered (e.g. as compared to the use of appetite suppressant or the like). A subject may typically take the collagen hydrolysate before the food craving manifests itself and thereby more effectively prevent and/or treat food craving. In accordance with the foregoing, the collagen hydrolysate as disclosed herein may be administered at various, preferred moments of the day whereby it has less effect on the normal intake of meals. For example, the collagen hydrolysate may be administered early in the morning and/or before or during breakfast. In addition or alternatively, the collagen hydrolysate may be administered late in the evening, such as before going to bed, or during or after dinner.

In a preferred embodiment, the use of collagen hydrolysate as disclosed herein comprises administering the collagen hydrolysate 2 hours or more, preferably 4 hours or more, more preferably 6 hours or more, prior to a meal.

In a preferred embodiment, the use of collagen hydrolysate as disclosed herein comprises repeatedly administering the collagen hydrolysate to a subject.

In a preferred embodiment, the repeatedly administering of collagen hydrolysate as disclosed herein is:

every day; and/or for at least one consecutive weeks, preferably for at least two consecutive weeks, more preferably at least four consecutive weeks.

In certain subjects, food craving may manifest itself consistently at a certain time and/or moment of the day. The inventors consider that the prevention and/or treatment of food craving by collagen hydrolysate is more effective when it is administered well before the time and/or moment of the day when food craving consistently occurs in a subject. For example, if a subject typically experiences food craving between 10-11 pm, the collagen hydrolysate is preferably administered no later than between 8-9 pm, or no later than between 6-7 pm, or no later than 4-5 pm, or in the morning (e.g. before or during breakfast).

In a preferred embodiment, the collagen hydrolysate as disclosed herein is administered 2 hours or more, preferably 4 hours or more, more preferably 6 hours or more, such as 8 hours or more, or 12 hours or more, prior to the time of the day when food craving typically manifests in a subject.

In a preferred embodiment, the collagen hydrolysate as disclosed herein is administered:

in the morning, such as before or during breakfast; and/or in the evening, such as during or after dinner.

The inventors found that repeated daily intake of collagen hydrolysate leads to the prevention and/or treatment of food craving. In accordance with the foregoing, the collagen hydrolysate is preferably administered for at least 2, 3, 4, 5, 6, 7, 10, or 14 days, wherein the days are preferably consecutive days, before the prevention and/or treatment of food craving is effected or most effective.

In a preferred embodiment, the prevention and/or treatment of food craving by the collagen hydrolysate as disclosed herein is effected by repeated daily administration of the collagen hydrolysate, preferably by daily administrations for at least 2 consecutive days, more preferably by daily administrations for at least 4 consecutive days, most preferably by daily administrations for at least 7 consecutive days.

Dosing of Collagen Hydrolysate Administration or Intake

In different embodiments, the daily dose of the collagen hydrolysate as disclosed herein is at least 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200, all in g, wherein the daily dose is the total dry weight amount administered to a subject per day. In addition or alternatively, in different embodiments, the daily dose of the collagen hydrolysate as disclosed herein is no more than 200, 190, 180, 170, 160, 150, 140, 130, 120, 110, 100, 95, 90, 85, 80, 75, 70, 65, 60, 55, 50, 45, 40, 35, 30, 25, 20, 15, 10, 5, or 1, all in g, wherein the daily dose is the total dry weight amount administered to a subject per day.

In a preferred embodiment, the use of collagen hydrolysate as disclosed herein comprises administering the collagen hydrolysate in an amount of between 1 g and 200 g, or between 1 g and 100 g, or between 2 g and 50 g, or between 5 g and 25 g, wherein the daily dose is the total dry weight amount administered to a subject per day.

It is beneficial in the context of the current invention if the daily dose of collagen hydrolysate does not exceed a certain threshold amount, in order not to reduce the normal appetite and/or to achieve a more specific reduction in craving. For example, a daily dose of 20 g collagen hydrolysate is preferred over a daily dose of 100 g collagen hydrolysate in healthy individuals, because the intake of 100 g appears to affect the normal appetite and intake of the normal meals (particularly lunch, dinner).

In a preferred embodiment, the use of collagen hydrolysate as disclosed herein comprises administering the collagen hydrolysate at a daily dose in an amount of 2-200 g, preferably 5-100 g, more preferably 10-50 g, wherein the amount is the dry weight amount of collagen hydrolysate.

In different embodiments, the unit dose of collagen hydrolysate as disclosed herein is in an amount of at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, 150, 160, 170, 180, 190, or 200, all in g, wherein the amount is the dry weight amount of collagen hydrolysate. In addition or alternatively, in different embodiments, the unit dose of collagen hydrolysate as disclosed herein is in an amount of no more than 200, 190, 180, 170, 160, 150, 140, 130, 120, 110, 100, 95, 90, 85, 80, 75, 70, 65, 60, 55, 50, 45, 40, 35, 30, 25, 20, 15, 14, 13, 12, 11, 10, 9, 8, 7, 6, 5, 4, 3, 2, or 1, all in g, wherein the amount is the dry weight amount of collagen hydrolysate.

In an embodiment, the collagen hydrolysate as disclosed herein is administered in a unit dose in an amount of between 0.5 g and 200 g, or between 1 g and 100 g, or between 2 g and 50 g, or between 5 g and 25 g, or between 5 and 15 g, wherein the amount is the dry weight amount of collagen hydrolysate.

In a preferred embodiment, the use of collagen hydrolysate as disclosed herein comprises administering the collagen hydrolysate at a unit dose in an amount of 2-50 g, preferably 5-25 g, more preferably 5-15 g, wherein the amount is the dry weight amount of collagen hydrolysate.

It is beneficial in the context of the current invention if the daily dose of collagen hydrolysate is divided into multiple unit doses (e.g. 2, 3, or 4 unit doses) in order not to reduce the normal appetite and/or to achieve a more specific reduction in craving. For example, intake of the daily collagen hydrolysate dose as a single dose appears to affect the appetite and intake of the normal meals (in particular lunch, dinner), which is unfavourable in healthy individuals.

The daily dose of collagen hydrolysate may be administered as a single unit dose, or as two, three, four or more unit doses. The two or more unit doses may be equal or different in amount. The daily dose of collagen hydrolysate as disclosed herein is preferably administered as two unit doses, more preferably as two unit doses each corresponding to 30-70%, preferably 40-60% of the daily dose amount.

In an embodiment, the two or more unit doses as disclosed herein are administered at least 1, 2, 3, 4, 5, 6, 7, 8, 9, 10, 11, or 12 hours separated from each other.

In a preferred embodiment, the dosage regimen for collagen hydrolysate as disclosed herein comprises administering the daily dose of collagen hydrolysate as two unit doses, wherein:

each unit dose is in an amount of 5-25 g, preferably 5-15 g, wherein the amount is the dry weight amount of collagen hydrolysate; and/or the two unit doses are administered at least 6 hours, preferably 8 hours, more preferably 12 hours separated from each other.

In a preferred embodiment, the daily dose of collagen hydrolysate is administered as two or more unit doses, wherein:

each unit dose is in an amount of 5-25 g, preferably 5-15 g, wherein the amount is the dry weight amount of collagen hydrolysate; and/or the two or more unit doses are administered at least 6 hours, preferably 8 hours, more preferably 12 hours separated from each other.

In a preferred embodiment, the collagen hydrolysate as disclosed herein is administered together with a meal.

In an embodiment, the dosage regimen for collagen hydrolysate comprises administering the daily dose of collagen hydrolysate as two unit doses, wherein one unit dose is administered in the morning (e.g. before or during breakfast) and one unit dose is administered in the evening (e.g. during or after dinner or before going to bed).

In a preferred embodiment, the dosage regimen for collagen hydrolysate as disclosed herein comprises administering collagen hydrolysate at least once a week.

It is beneficial in the context of the current invention if the daily dose of collagen hydrolysate is administered frequently, e.g. daily or every other day other. In comparison, intake of collagen hydrolysate only once a week is less/not effective in reducing craving.

In a preferred embodiment, the dosage regimen for collagen hydrolysate as disclosed herein comprises administering collagen hydrolysate every day or every other day.

In a preferred embodiment, the collagen hydrolysate is administered every day or every other day.

In a preferred embodiment, the dosage regimen for collagen hydrolysate as disclosed herein comprises administering collagen hydrolysate at least once a day.

In a preferred embodiment, the collagen hydrolysate is administered at least once a day.

It is beneficial in the context of the current invention if the daily dose of collagen hydrolysate is administered to a subject for more than one week, as more prolonged administration leads to highest reduction in craving.

In an embodiment, the dosage regimen for collagen hydrolysate as disclosed herein comprises administering collagen hydrolysate for at least 2 consecutive days, preferably for at least 4 consecutive days, more preferably for at least 7 consecutive days.

In an embodiment, the dosage regimen for collagen hydrolysate as disclosed herein comprises administering collagen hydrolysate for at least 2 consecutive weeks, preferably for at least 4 consecutive weeks, more preferably for at least 8 consecutive weeks.

In a preferred embodiment, the dosage regimen for collagen hydrolysate as disclosed herein comprises administering collagen hydrolysate for at least one week, preferably for at least two consecutive weeks, more preferably for at least four consecutive weeks.

General Definitions

The term "unit dose" as used herein relates to the amount of a compound, substance, or composition taken by a subject in a single dose. The unit dose typically is in a pre-prepared form (e.g. prepacked dosage) ready for administration. The unit dose may for example (also) be identifiable from the product packaging or label. The daily dose can be divided into multiple unit doses.

The terms "administer" or "administration" as used herein comprise providing a compound, substance, or composition to a subject consuming it. A subject consuming a compound, substance, or composition may administer it to himself/herself. In such a case the term "administer" can be read as "take in".

As used herein, "preventing", or "prevention" means to ensure that a subject will not develop a condition (e.g. selective hunger). An intervention is herein also considered to be preventive when a condition is delayed, reduced in severity and/or reduced in incidence, even when the condition is not entirely kept from happening. As used herein, "preventing" or "prevention" by an intervention encompasses the situation wherein a subject previously has experienced a condition, but an intervention keeps the condition from recurring. The "preventing" or "prevention" may have a therapeutic and/or a non-therapeutic effect. If the "preventing" or "prevention" is therapeutic in nature, it may be also directed at a symptom of a disease or condition and/or an underlying pathology thereof. The "preventing", or "prevention can be defined by any delay, change in severity, and/or change in incidence, such as of at least 5, 10, 20, 30, 40, 50, 60, 70, 80, 90, 100%, or any amount of change in between, as compared to a control or reference as measured by any standard technique.

As used herein, "treating" or "treatment" means that an intervention reduces, ameliorates, and/or cures a condition (e.g. food craving) once the condition is already existing. The terms "reducing", "decreasing" and "ameliorating" may be used interchangeably together with the term "treating" when describing a change in the condition. The "treating" or "treating" may have a therapeutic and/or a non-therapeutic effect. If the "treatment' or "treating" is therapeutic in nature, it may be directed at a symptom of a disease or condition and/or an underlying pathology thereof. The treatment can for example be any reduction in severity, incidence, and/or frequency of the condition, such as of at least 5%, 10%, 20%, 40%, 50%, 60%, 80%, 90%, 95%, or 100%, or any value in between, as compared to a control or reference as measured by any standard technique. In the current disclosure, "treating" or "treatment" of food craving preferably refers to "treating" or "treatment" the incidence, frequency and/or severity of food craving. As used herein, "treating" also encompasses "curing".

As used herein, the term "subject" refers to any animal that may experience food craving. Typically, the term "subject" is used in reference to a human.

The term "symptom" as used herein relates to any physical (e.g. a reduced function), mental (e.g. pain), or biological feature (e.g. a biochemical or histological change in a bodily tissue) which is regarded as indicating a condition of a disease. A symptom may be experienced by a subject having the symptom, or in addition or alternatively, may be diagnosed or measured as part of a diagnostic process.

The term "healthy" as used herein refers to good physical or mental condition. A "healthy" subject as used herein is a subject that is not suffering a pathological condition related to excessive food craving. In addition, a "healthy" subject herein does not experience symptoms of pain and suffering related to food craving which requires a medical treatment.

A "healthy" subject may be any subject wherein the prevention and/or treatment of food craving is not considered to cause a therapeutic effect.

As used herein, "satiation" refers to the amelioration of a desire to eat after consumption of food, generally during or after consumption of a meal. Satiation makes a person feel full, who generally as a result will stop eating.

As used herein, "satiety" refers to a physical feeling of fullness that allows a subject to stop eating for a certain period of time. Satiety typically influences the time between two meals meal, as it may put off the feeling of getting hungry.

The terms 'comprising' or 'to comprise' and their conjugations, as used herein, refer to a situation wherein said terms are used in their non-limiting sense to mean that items following the word are included, but items not specifically mentioned are not excluded. It also encompasses the more limiting verb 'to consist essentially of' and 'to consist of'.

Reference to an element by the indefinite article 'a' or 'an' does not exclude the possibility that more than one of the elements is present, unless the context clearly requires that there be one and only one of the elements. The indefinite article 'a' or 'an' thus usually means 'at least one'.

As used herein, a level is "increased" or "decreased" when it is at least 1%, such as 5%, 10%, 15%, 20%, 25%, 30%, 35%, 40%, 45%, or 50% higher or lower, respectively, than the corresponding level in a control or reference. Alternatively, a level in a sample may be considered increased or decreased when it is statistically significantly higher or lower, respectively, compared to a level in a control or reference (including an earlier time point). The term "to reduce" may herein be used interchangeably with "to decrease". The term "reducing" may herein be used interchangeably with "decreasing".

The term "consecutive" or "consecutively" as used herein in the context of collagen hydrolysate administration herein means that the administrations follow one another in order without gaps in a given time period. For example, when "collagen hydrolysate is administered for 4 consecutive days", this means that the collagen hydrolysate is administered for at least once a day for 4 days in a row (e.g. on Monday, Tuesday, Wednesday, and Thursday of the same week), irrespective of the number of administrations per day or the total number of administrations. For example, when "collagen hydrolysate is administered for 4 consecutive weeks", this means that the collagen hydrolysate is administered for at least once a week for 4 weeks in a row, irrespective of the number of administrations per day, the number of administrations per week or the total number of administrations.

FIGURE LEGENDS

FIG. 1. Average craving score reported by individuals at baseline, 4 weeks, and 8 weeks after collagen hydrolysate supplementation.

EXPERIMENTAL EXAMPLE

Example 1

Aim

A study was conducted to determine the effect of daily collagen hydrolysate supplementation on food craving in healthy women.

Method

Fourteen healthy women (body mass index>25 kg/m$^2$; age 35-65) not following any other dietary or lifestyle interventions participated in the study. None of the participants had medical conditions or were on medication.

The participants received daily supplementation of 20 g dietary collagen hydrolysate (Peptan, B 5000, bovine origin) for 8 weeks. The daily dose was divided into two unit doses of 10 g. One unit dose was taken in the morning, typically early in the morning before breakfast. One unit dose was taken in the late afternoon, or in the evening with or after dinner.

Participants were asked to fill out a Medical Symptom Questionnaire (MSQ) at baseline, at 4 weeks and at 8 weeks. In the MSQ, participants were asked to indicate whether food craving was experienced in the 48 hours prior to filling out the MSQ. For this purpose, the following point scale system was provided in the MSQ:

0—Never or almost never have the symptom
1—Occasionally have it, effect is not severe
2—Occasionally have it, effect is severe
3—Frequently have it, effect is not severe
4—Frequently have it, effect is severe At the end of the study, the participants were interviewed. The interview was aimed at determining in addition to the MSQ, among others:

if a reduction in food craving had occurred, when the reduction was first seen after commencing the daily collagen hydrolysate supplementation;

if a reduction in food craving had occurred, whether the reduction was mostly due to a reduction in the frequency or severity of food craving;

whether participants experienced a change in their normal food routine;

whether there was a correlation between the timing of collagen hydrolysate intake and the reduction in food craving;

whether daily collagen hydrolysate supplementation caused possible side effects.

Result

The average craving score was reduced from 3.1 at baseline to 2.4 at both 4 weeks and 8 weeks (FIG. 1). The reductions in food craving were statistically significant (p-value<0.05) based on a paired t test. Eleven out of fourteen participants (79%) showed at least one point reduction in the food craving score during the study as compared to baseline.

The interview established the following:

a reduction in food craving was most typically seen in the first week after commencing the daily collagen hydrolysate supplementation. In most individuals, the reduction in food craving started in the third or fourth day after commencing the daily collagen hydrolysate supplementation;

a reduction in food craving was due to a reduction in frequency and/or severity of food craving, most typically due to a reduction in frequency of food craving;

the participants generally did not experience noticeable change in their normal food routine;

there is no clear correlation between the timing of collagen hydrolysate intake and the reduction in food craving. For example, a reduction in food craving was also observed when there was several hours delay between collagen hydrolysate intake and the moment when food craving normally occurred. A reduction in food craving during the day was observed in participants taking collagen hydrolysate early in the morning and late in the evening.

the daily collagen hydrolysate supplementation did no cause side effects.

Conclusion

Collagen hydrolysate reduces food craving in healthy individuals. The reduction in food craving by collagen hydrolysate was found to be durable, based on the finding that the effect is seen at both 4 weeks and 8 weeks after commencing supplementation. It was found that the reduction in food craving due to collagen hydrolysate is not necessarily a direct effect on hunger or increased satiation. First, repeated daily intake of collagen hydrolysate was found to help in reducing food craving. Second, participants generally did not experience a noticeable change in their normal food routine. Third, no clear correlation could be established between the timing of collagen hydrolysate intake and the reduction in food craving. The daily intake of 20 g collagen hydrolysate did not cause side effects and is considered to be a safe approach for reducing food craving.

Example 2

Aim

It is studied how the collagen hydrolysate dose and administration regime affects craving and the normal appetite for meals in healthy individuals.

Method

Female participants (inclusion criteria according to Example 1) receive collagen hydrolysate as supplement (Peptan, B 5000, bovine origin).

A comparison is made between participants receiving a total daily dose of collagen hydrolysate of 20 g or 100 g. The daily dose is divided over two unit doses, one taken in the morning and one taken in the afternoon or evening.

A comparison is made between a collagen hydrolysate daily dose (20 g) provided as single unit dose (1×20 g) or as multiple unit doses divided over the day (2×10 g). This is also compared to a collagen hydrolysate daily dose of 40 g, provides as four unit doses (i.e. 4×10 g) divided over the day.

A comparison is made between collagen hydrolysate intake (2×10 g unit dose daily), for a period of 1 week or 8 weeks.

A comparison is made between intake of collagen hydrolysate (2×10 g unit dose daily) daily, every other day, or once a week.

To determine the effect of the dosage regimen on craving, the following point scale system is used:

0—Never or almost never have craving
1—Occasionally have craving, effect is not severe
2—Occasionally have craving, effect is severe
3—Frequently have craving, effect is not severe
4—Frequently have craving, effect is severe To determine the effect of the dosage regimen on changes in normal appetite for meals, the following point scale system is used:

0—Never or almost never have reduced appetite
1—Occasionally have a reduced appetite, effect is not severe
2—Occasionally have a reduced appetite, effect is severe
3—Frequently have a reduced appetite, effect is not severe
4—Frequently have a reduced appetite, effect is severe Results The results are summarized in Table 1.

A unit dose of 20 g or 100 g both reduces craving. However, the 100 g unit dose also reduces the normal appetite and lower intake of meals and is therefore less favourable, for instance in healthy normal weight individuals that are not necessarily seeking weight reduction.

Intake of two or more unit doses of collagen hydrolysate reduces craving more effectively than intake of the same daily amount as a single unit dose. Intake of (a relatively large) single unit dose affects the normal appetite more and can therefore be less favourable under certain circumstances. Similar results are obtained if the collagen hydrolysate is administered as 2×10 g, 4×5 g, or 4×10 g. Dividing total intake into multiple unit doses is particularly more beneficial when the total daily dose increases. The specific reduction in craving is highest if each unit dose is not more than 20 g, e.g. around ~10 g.

Daily intake of collagen hydrolysate for one week also reduces craving without affecting the normal appetite, however intake of collagen hydrolysate for 8 weeks shows the highest specific reduction in craving.

A particularly strong reduction in craving is seen when collagen hydrolysate is taken daily or every other day, but (hardly) any reduction in craving is seen if collagen hydrolysate is taken once per week.

Overall, the specific reduction in craving is highest when the dose of collagen hydrolysate does not exceed a certain threshold amount (e.g. around 20 or 40 g daily dose), and preferably divided over two or more unit doses. Moreover, the specific reduction in craving is highest when the collagen hydrolysate is taken once every other day or every day. These parameters in administration regimen allow for specific lowering of craving, without affecting the normal appetite and normal food intake.

TABLE 1

Effect of collagen hydrolysate administration regime on reduction in craving and normal appetite in healthy participants.

| Daily dose | No. unit doses | Administration scheme | Duration (weeks) | Reduction in craving | Reduction in normal appetite |
|---|---|---|---|---|---|
| 20 g | 2 | Daily | 8 | High | No |
| 40 g | 4 | Daily | 8 | High | No |
| 100 g | 2 | Daily | 8 | High | Yes |
| 20 g | 1 | Daily | 8 | Average | Yes |
| 20 g | 2 | Daily | 1 | Average | No |
| 20 g | 2 | Once every other day | 8 | High | No |
| 20 g | 2 | Once per week | 8 | Low | No |

Conclusion

Overall, a specific reduction in craving (i.e. without affecting normal appetite) is highest when the dose of collagen hydrolysate is not too high (e.g. 20 or 40 g daily dose), and divided over two or more unit doses, e.g. each not more than 20 g, such as ~10 g. Moreover, a specific reduction in craving is highest when the collagen hydrolysate is taken once every other day or daily.

Example 3

Aim

A comparison is made between a collagen hydrolysate average molecular weight of ~2000 Da, ~5000 Da or ~9000 Da in reducing craving.

Method

Female participants (inclusion criteria according to Example 1) receive a daily dose of 20 g collagen hydrolysate for a period of 8 weeks. The daily dose is divided over two unit doses, one taken in the morning and one taken in the afternoon or evening.

The reduction in craving is measured according to Examples 1 and 2.

Results

A specific reduction in craving is seen for the collagen hydrolysate for all average molecular weights tested, but the highest reduction in craving is seen when the average molecular weight of the collagen hydrolysate is around ~2000 or ~5000 Da.

Conclusion

Collagen hydrolysate with an average molecular weight below 9000 Da leads to highest specific reduction in craving. Without being bound by theory, based on the current findings, the present inventors consider that a larger molecular weight creates a larger feeling of fullness and therefore leads to larger suppression of normal appetite, without further inhibition of craving.

The invention claimed is:

1. A method for reducing food craving independent of normal appetite, comprising administering collagen hydrolysate to a subject, wherein the collagen hydrolysate has a weight average molecular weight of below 9000 Da, wherein the administering the collagen hydrolysate to the subject involves:

i) administering the collagen hydrolysate every day or every other day; and ii) administering a total daily dose of collagen hydrolysate of 15-60 g/day as one or more unit doses, wherein each unit dose is not more than 20 g, wherein the dose amount is the dry weight amount of collagen hydrolysate.

2. The method according to claim 1, wherein the food craving is for calorie-dense foods, wherein calorie-dense foods are defined as foods containing more than 200 kcal per 100 g weight.

3. The method according to claim 1, wherein the food craving is characterised by a preference for calorie-dense foods over non-calorie-dense foods, wherein calorie-dense foods are defined as foods containing more than 200 kcal per 100 g weight.

4. The method according to claim 1, wherein the food craving is characterised by a preference for calorie-dense foods over nutrient-rich foods, wherein calorie-dense foods are defined as foods containing more than 200 kcal per 100 g weight, wherein nutrient-rich foods are defined as foods having a median Nutrient Rich Food (NRF) 9.3 Index score of more than 0.

5. The method according to claim 2, wherein the calorie-dense foods are further defined as foods with more than 10 g sugar per 100 g weight of the food.

6. The method according to claim 2, wherein the calorie-dense foods are further defined as foods with more than 10 g saturated fat per 100 g weight of the food.

7. The method according to claim 1, wherein the food craving is for a food selected from the group consisting of processed food, fried food, potato fries, pizza, candy, chips, pastry, cake, ice-cream, chocolate, fast-food, nuts, butter, cream, cheese, bacon, sausages, sauces, condiments, dressings and sugary drink.

8. The method according to claim 1, wherein the food craving is in the evening and/or night.

9. The method according to claim 1, wherein the collagen hydrolysate has a weight average molecular weight between 1500 Da and 6000 Da.

10. The method according to claim 1, wherein the daily dose is administered as two or more unit doses of 5-15 g, wherein the amount is the dry weight amount of collagen hydrolysate.

11. The method according to claim 1, wherein the daily dose of collagen hydrolysate is administered as two or more unit doses, wherein the two or more unit doses are administered at least 6 hours separated from each other.

12. The method according to claim 1, wherein the daily dose of collagen hydrolysate is administered as two or more unit doses, wherein the two or more unit doses are administered at least 8 hours or 12 hours separated from each other.

13. The method according to claim 1, wherein the collagen hydrolysate is administered for at least 2 consecutive days.

14. The method according to claim 1, wherein the collagen hydrolysate is administered for at least 4 or at least 7 consecutive days.

15. The method according to claim 1, wherein the collagen hydrolysate is administered for at least 2 consecutive weeks.

16. The method according to claim 1, wherein the collagen hydrolysate is administered for at least 4 consecutive weeks or at least 8 consecutive weeks.

17. The method according to claim 1, wherein the collagen hydrolysate is administered together with a meal.

18. The method according to claim 1, wherein the collagen hydrolysate is provided in a food formulation, food supplement formulation, or pharmaceutical formulation.

19. The method according to claim 1, wherein the collagen hydrolysate is derived from a collagen obtained from a tissue selected from the group consisting of skin, cartilage, bone, tendon, ligament, connective tissue, and combinations thereof.

20. The method according to claim 1, wherein the collagen hydrolysate is derived from a collagen selected from the group consisting of porcine collagen, bovine collagen, and fish collagen.

* * * * *